United States Patent [19]

Rand et al.

[11] Patent Number: 5,442,673
[45] Date of Patent: Aug. 15, 1995

[54] FIXED SEPTUM COLLIMATOR FOR ELECTRON BEAM TOMOGRAPHY

[75] Inventors: Roy E. Rand, Palo Alto; Patrick B. Halahan, San Mateo, both of Calif.

[73] Assignee: Siemens Aktiengesellschaft, Munich, Germany

[21] Appl. No.: 220,076

[22] Filed: Mar. 30, 1994

[51] Int. Cl.⁶ .............................................. A61B 6/02
[52] U.S. Cl. ........................................ 378/10; 378/4; 378/150
[58] Field of Search ...................... 378/10, 4, 9, 19, 21, 378/22, 25, 145, 147, 150, 160

[56] References Cited

U.S. PATENT DOCUMENTS

| | | | |
|---|---|---|---|
| 4,045,672 | 8/1977 | Watanabe | 378/10 |
| 4,122,346 | 10/1978 | Enge | 378/10 X |
| 4,130,759 | 12/1978 | Haimson | 378/10 |
| 4,135,095 | 1/1979 | Watanabe | 378/10 X |
| 4,203,036 | 5/1980 | Tschunt | 378/10 X |
| 4,274,005 | 6/1981 | Yamamura et al. | 378/10 X |
| 4,352,021 | 9/1982 | Boyd et al. | 378/12 |
| 4,461,016 | 7/1984 | Weiss et al. | 378/25 X |
| 4,610,021 | 9/1986 | Peschmann et al. | 378/150 |

FOREIGN PATENT DOCUMENTS 7803065  3/1978  Netherlands ................. 378/10

Primary Examiner—David P. Porta
Attorney, Agent, or Firm—Lawrence C. Edelman

[57] ABSTRACT

An x-ray collimator is described which is useful in an electron beam (EB) computed tomography (CT) scanner of the type in which a rotating electron beam is directed to impinge upon a ring-shaped target and the x-rays generated in response thereto are directed to a ring shaped detector array spaced therefrom. The collimator consists of an x-ray blocking septum having an aperture therein, the septum being located in a fixed position substantially co-planer with the planes of the target and the detector, so as to block all x-rays directed from said target to said detector except those which pass through said aperture. Tomographic slice width is determined by the "view" from the spot where the electron beam impinges upon the target, through the aperture, to the detector, and is variable by adjusting the position where the electron beam impinges upon the width of the x-ray target, and in a preferred embodiment, the position of a movable ring. In the preferred embodiment, a movable ring is provide which has a longitudinal axis positioned coaxial with the axis of the aperture and an end face opposed to and parallel with the septum. As well as forming part of the collimator, this ring acts as a pre-collimation radiation shield. This ring is moved concurrently when moving the position where the electron beam impinges upon the width of the x-ray target when the tomographic slice width is varied, by adjusting the spacing between the end face of the moveable ring and the septum.

18 Claims, 4 Drawing Sheets

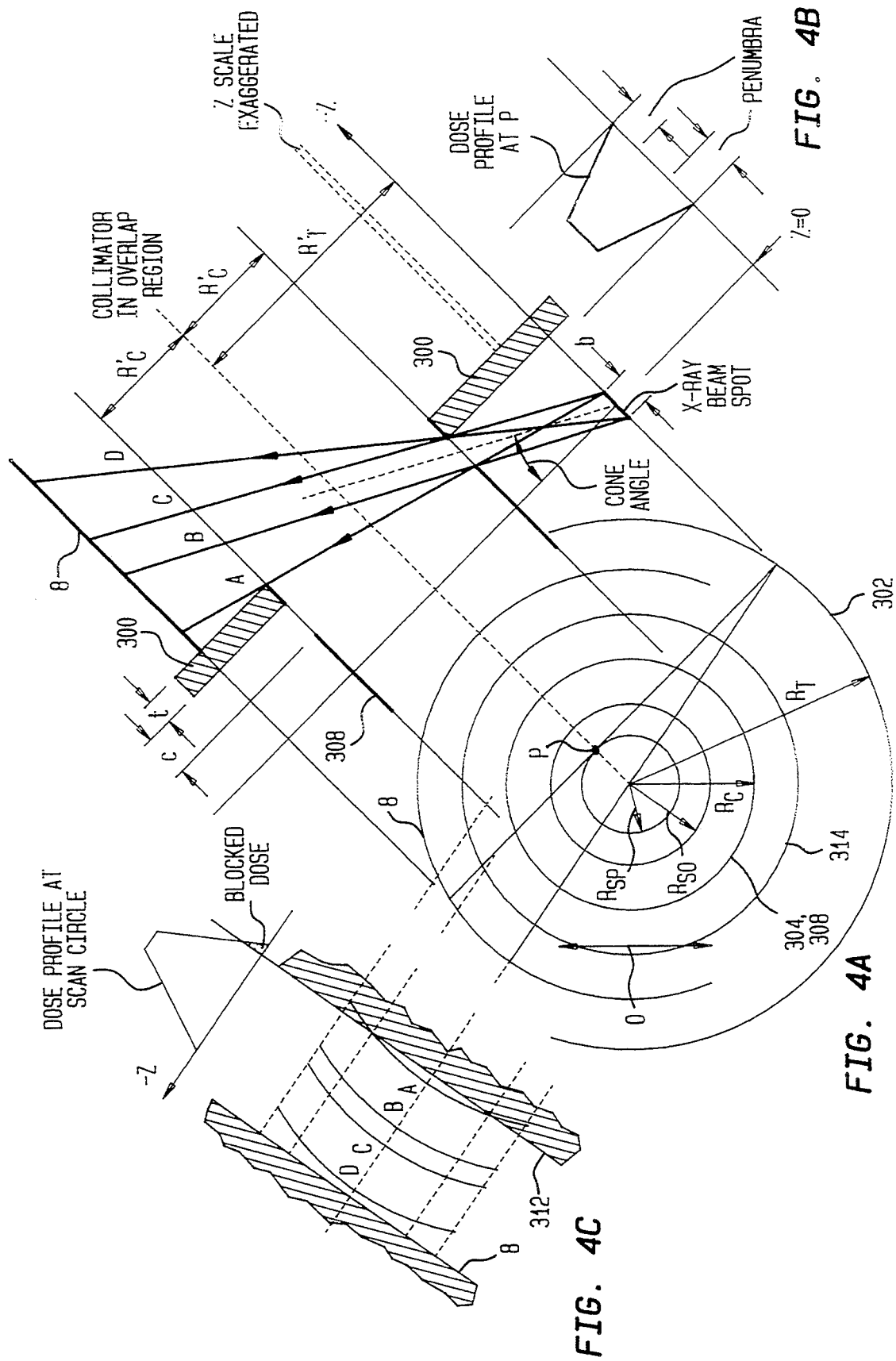

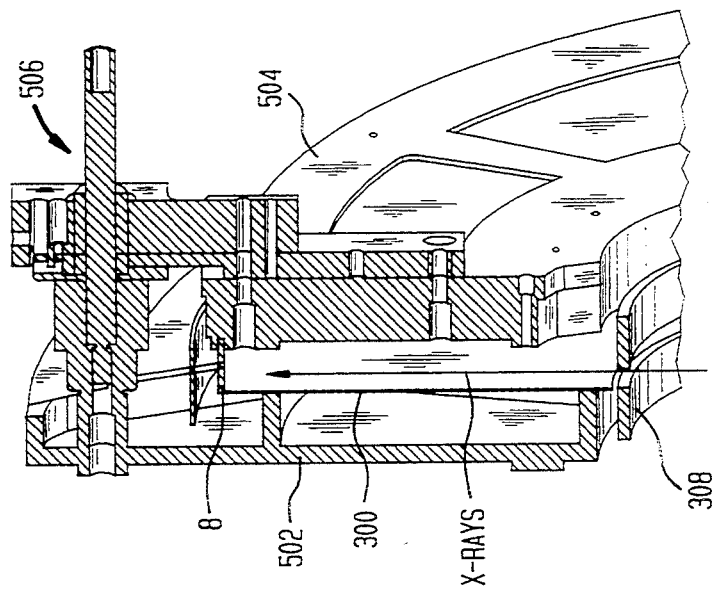
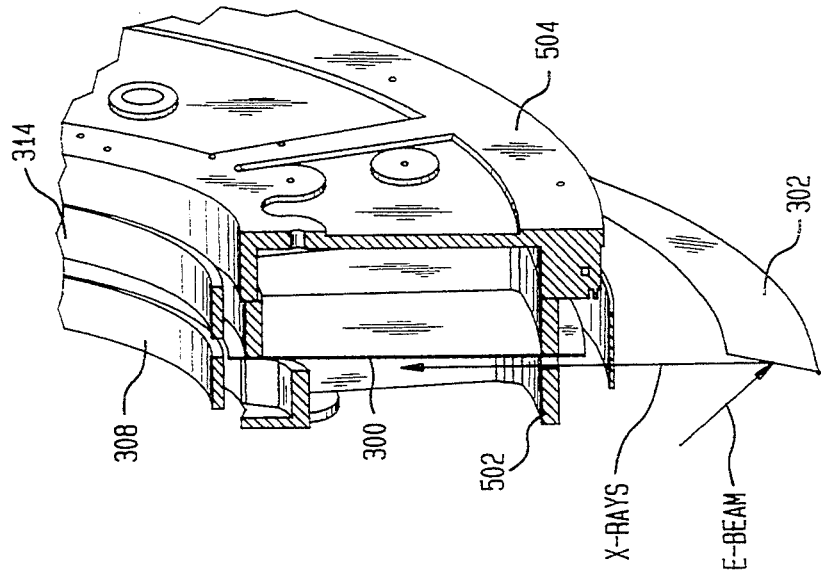
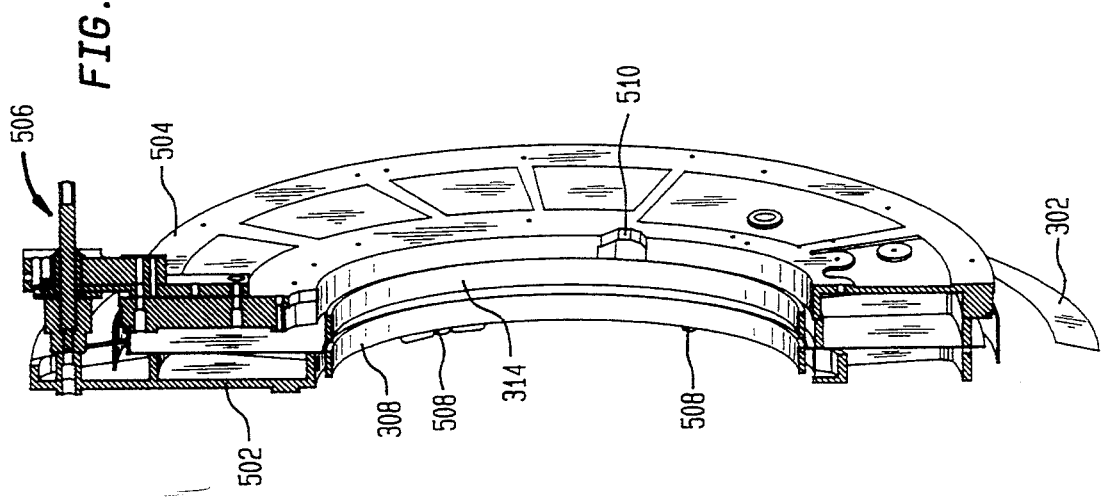

FIXED SEPTUM COLLIMATOR FOR ELECTRON BEAM TOMOGRAPHY

BACKGROUND OF THE INVENTION

1. Field of the Invention

The present invention relates to an x-ray collimator for use in an electron beam computed tomography scanner, and more particularly, to an x-ray collimator formed using a fixed position x-ray blocking septum having an aperture therein. In a preferred embodiment a movable ring is also provided having a longitudinal axis positioned coaxially with the aperture in the septum.

2. Description of the Prior Art

In computed tomography (CT) scanners having a scanning electron beam x-ray source, an electron beam is magnetically deflected so as to rotate in a generally circular path, and in doing so, impinge upon a ring-shaped target, thereby generating a rotating source of x-rays. After passing through a collimator, the x-rays are shaped into a fan beam and then intercepted by a ring-shaped detector array which overlaps the collimator. U.S. Pat. No. 4,352,021 issued Sep. 28, 1982 discloses such an electron beam scanner, which scanners are commercially available, e.g., from Imatron, Inc., located in South San Francisco, Calif. In order to collimate the x-rays emitted from a ring-shaped target, prior art collimators have been formed by fixing on a plastic cylinder first and second metallic rings having a defined space therebetween, which space establishes the x-ray fan beam and defines a given slice width. In order to change the slice width, a second set of metallic rings having a different defined space therebetween are provided on another portion of the plastic cylinder, which is spaced away from the first set. The second set effectively comprises a new collimator which must be mechanically substituted for the first collimator. The substitution is accomplished by positioning the second set of rings over the target in order to establish the new collimator.

The forenoted prior art collimator arrangement is relatively expensive due to the mechanical construction of multiple sets of collimators and the mechanical adjusting arrangements which are necessary in order to accurately position the appropriate set of collimator rings with respect to the target ring and the detector array. Additionally, the slice (or x-ray fan beam) width is fixed by the position established between the different sets of collimator rings and is therefore not continuously variable.

It would be desirable to provide a lower-cost collimator assembly useful for electron beam (EB) computed tomography (CT) scanners.

It would be even more desirable to provide such a lower-cost collimator which would provide improved performance.

SUMMARY OF THE INVENTION

Apparatus for collimating a moving source of x-rays, comprising a fixed position x-ray blocking septum located in a space between a source of the moving x-rays and an x-ray detector array for detecting the x-rays. The septum is positioned substantially parallel with respect to a plane described by the moving source, so as to divide the space into target and detector sections, respectively, the target section including the source of moving x-rays and the detector section including the x-ray detector array. The septum has an aperture therein through which a portion of the x-rays pass from the source to the detector array, thereby collimating the x-rays.

BRIEF DESCRIPTION OF THE DRAWINGS

FIG. 4a is a schematic illustration of an end view of portions of the system of FIG. 1, and FIGS. 4b and 4c illustrate different projections of the view of FIG. 4a, useful for showing the x-ray blocking performance of the collimator of FIG. 3.

FIGS. 5(a), (b) and (c) illustrate in greater detail mechanical aspects of the collimator arrangement of FIG. 3.

DESCRIPTION OF THE PREFERRED EMBODIMENTS

Figures 1, 2:
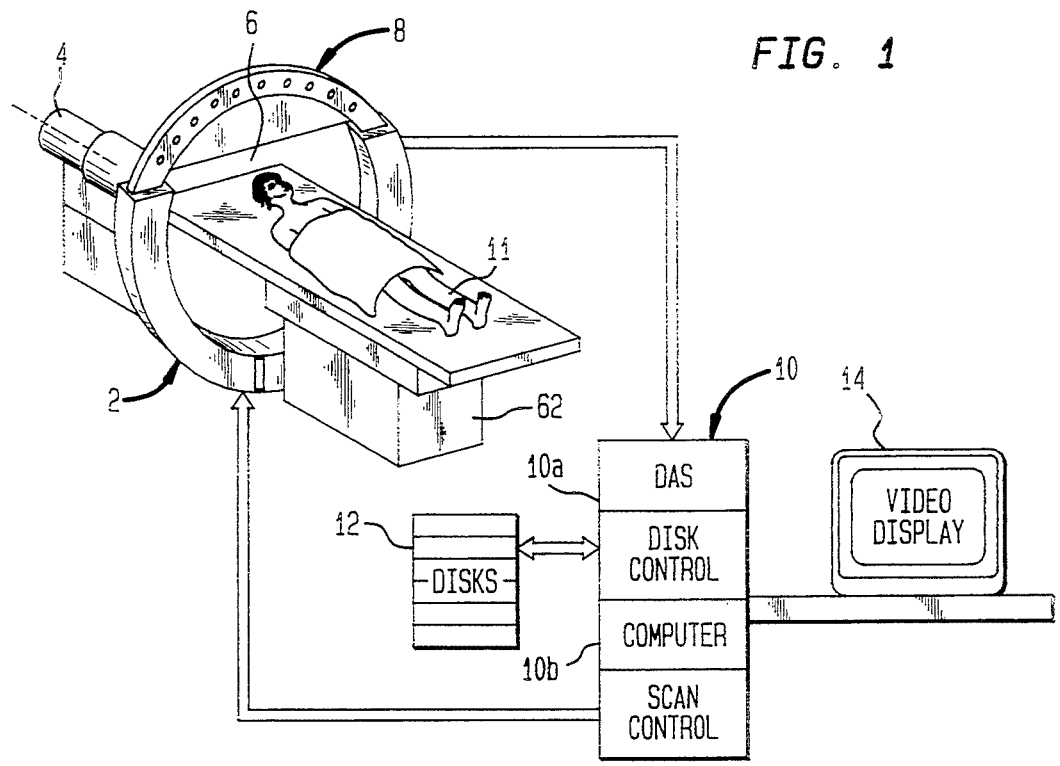
FIG. 1 illustrates an electron beam computed tomography scanner of the type incorporating a collimator (shown in FIG. 3) constructed in accordance with the principles of the present invention.
FIG. 2 is a cross-sectional view of the system of FIG. 1.

As shown in FIG. 1 the electron beam (EB) computed tomography (CT) scanner includes three major components; an electron beam scan tube 2 having a cylindrical portion 4 and a semi-circular conical portion 6; an x-ray detector array 8 and a computer system 10. The scan tube 2 develops and projects an electron beam towards a target ring which generates x-rays upon impingement of the electron beam. The x-rays, after being collimated and passing through a patient 11, are intercepted and detected by the detector array 8. The data output of the detector array is applied to a digital acquisition system (DAS) 10a of the computer system 10. Computer system 10 includes a plurality of storage disks 12 for recording the acquired detector data and holding it for later processing. Computer system 10 also includes a scan control portion 10b having an output which controls the scan tube and a video display 14 which presents tomographic images reconstructed by the computer system using the acquired detector data.

Referring more particularly to FIG. 2, the scanning and deflection system are shown in more detail. Scan tube 2 includes a vacuum envelope 20 which houses an electron gun 22 in the cylindrical portion 4. The electron gun projects an axial electron beam 23 along the semi-circular conical portion 6. Focus coils 24 magnetically focus the beam as a spot which impinges a semi-circular ring-shaped conical target 26 positioned so as to be angled 82° with respect to the longitudinal axis of scan tube 2. Bending coils 27 provide a magnetic field to bend the beam so that it passes through the semi-circular conical portion 6 of the tube on its path to target 26. A set of suitable cooling coils 28 may be imbedded within a target holder 29 and serves to cool target 26.

Bending coils 27 not only deflect the electron beam, as noted above, but also rapidly and repeatedly sweep it along target ring 26 so as to create a substantially planar rotating source of x-rays. A collimator assembly, (shown in FIGS. 3, 4 and 5) is disposed in the beam path between target ring 26 and detector array 8 so as to block the x-rays emitted by the target ring and define an x-ray beam projected as a one to ten millimeter thick planar fan beam. A sector of the fan beam is detected by a portion of x-ray detector array 8 which provides measured values in response thereto, which are applied to the DAS 10a of computer system 10 where they are used to reconstruct the tomographic image(s). The EB CT scanning system described above (except for the details of the collimator arrangement, to be described in detail next) is well known to those of ordinary skill in the art, and is commonly know as the ULTRAFAST CT scanner manufactured and sold by Imatron, Inc. Thus, no further description of the construction and operation of the basic system an its components is deemed necessary.

Figure 3:
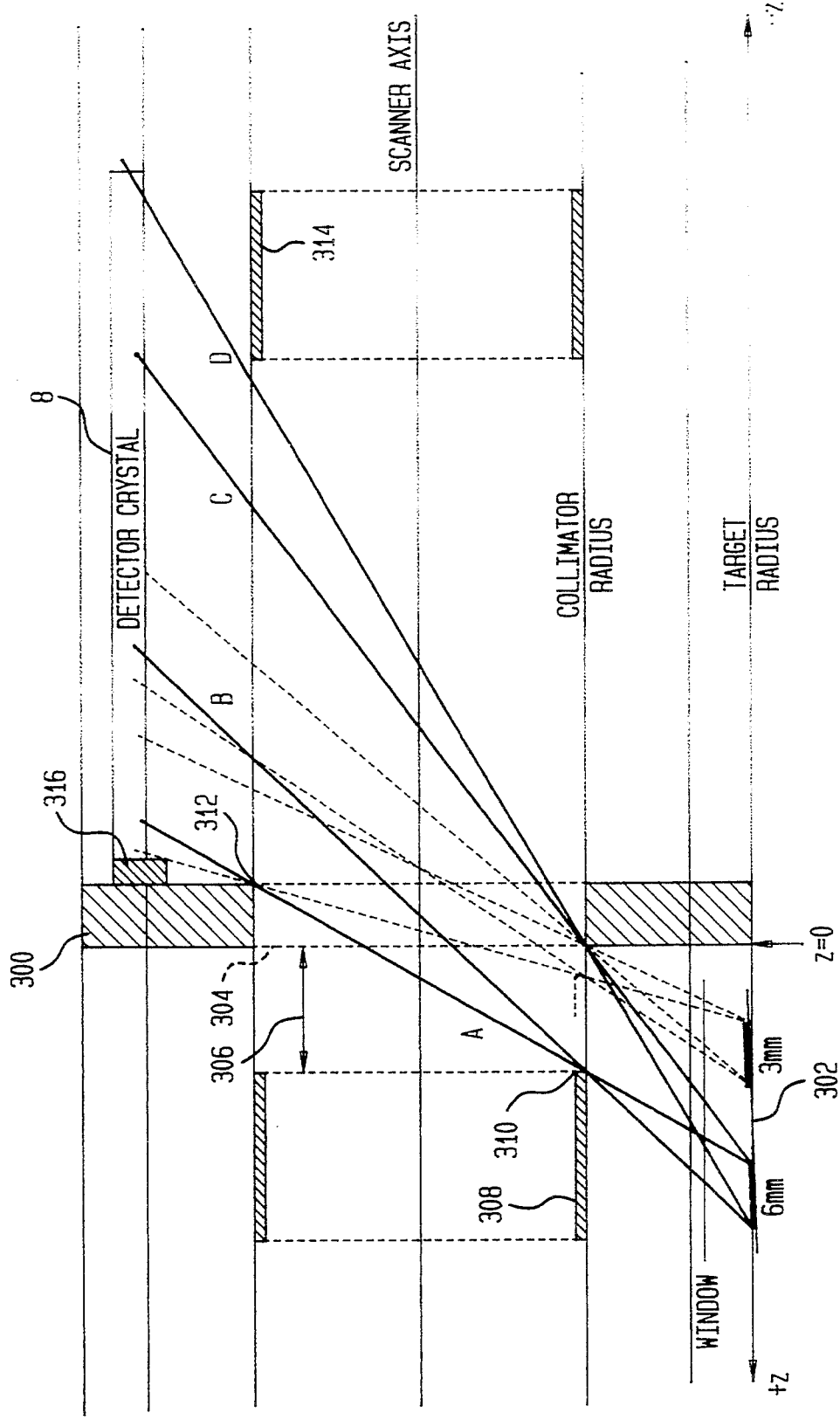
FIG. 3 is a schematic illustration of details of the collimator arrangement of the present invention as used in the system of FIG. 1.

The novel collimator is shown schematically in FIGS. 3–5, with identical portions of each of these figures using the same reference numbers. The design is based on an apertured x-ray blocking septum 300 fixed adjacent to the end face of vacuum chamber cone 6, or equivalently to a support housing which includes the detector array 8. The septum is generally in the form of a perforated disc positioned substantially parallel to and in a space between the plane defined by the moving source of x-rays on target 302 and the plane defined by the x-ray detector array 8, so that only those x-rays passing through its perforation (or aperture) 304 reach detector array 8. That is, septum 300, the moving source of x-rays on target 302 and detector array 8 are all positioned so as to be substantially parallel, yet spaced apart so that septum 300 forms an x-ray barrier between the moving source of x-rays on target 302 and detector array 8. Preferably, these planes are exactly parallel so as to minimize image distortion. (Note, the ratio of the horizontal to the vertical scales in FIGS. 3 and 4b and 4c is 100 to 1, in order to more clearly illustrate the principles involved in the present invention. However, note that this also results in a distortion of some of the illustrated angular relationships, such as the 82° angle of target 302 to the longitudinal axis of the scan tube.) The edge of septum 300 which faces the x-ray target 302 is illustrated as being at a point z=0, the nominal origin of the axial path of the scanner. At this point, the inner shoulder of aperture 304 of septum 300 defines one edge of a collimator slot 306. In the preferred embodiment the other edge of collimator slot 306 is defined by an end face 310 of an adjustable ring 308, the plane of end face 310 being positioned substantially parallel (and preferably exactly parallel) to the target side (left side of FIG. 3) of septum 300 and the longitudinal axis of ring 308 being substantially coaxial with the longitudinal axis of aperture 304. In the illustrated embodiment the outside diameter of ring 308 is substantially the same as the diameter of aperture 304, however, this relationship is basically a matter of system design. Thus, it is the space between ring 308 and septum 300, as "viewed" from the rotating x-ray source on target ring 302 which controllably defines the width for collimator slot 306. Furthermore, as evident from FIG. 3, ring 308 also serves a very important additional function, that is, as a pre-patient radiation shield which protects the patient so that he is only exposed to radiation which will actually form the collimated radiation beam. Additionally, ring 308 serves to reduce x-ray scattering (which can degrade image quality) and also improves the uniformity of the dose profile (as shown in FIG. 4b). Note, however, in an alternative embodiment wherein limitation of radiation exposure to the subject being imaged is not of concern, blocking of the x-rays prior to collimation, and hence collimator ring 308, although preferable, would not be necessary. In this case, the useful beam width would be defined solely by the "view" between target 302 and detector array 8, as defined by the +z position of the electron beam spot across the width of target 302. The axial z position of the beam spot is adjustable by appropriate control of bending coils 27 so as to move the electron beam on angled target 302 so as to be closer to or further away from septum 300. As the beam spot is moved closer toward septum 300, the "view" from target 302 to detector array 8 through aperture 304 is correspondingly decreased, thereby correspondingly decreasing the beam width so that slice widths from as wide as 10 mm to as small as 1 mm are currently achievable with minimum cone angle and maximum efficiency, as illustrated in FIG. 3. Additionally, it is noted that the novel collimator arrangement not only allows for a simple adjustment to achieve a change in the slice width, but that it allows the adjustment to be made, if desired, even during a scan sequence, and furthermore without the requirement of moving the detector array or the septum. Furthermore, in the preferred embodiment, adjustment of collimator ring 308 is made concurrently with adjustment of the axial position of the beam spot on the target, thereby continually maintaining its radiation blocking advantage for the patient.

As shown in FIG. 3, for a 6 mm slice width the optimum beam spot position is defined by a "z-ray" A which passes from the right edge of the "6 mm" slice beam spot position on the target 302 (i.e., a portion of the target ring which is furthest from septum 300), to the left edge of the collimator slot 306 (defined by end face 310 of adjustable ring 308) and then close to the right edge 312 of septum aperture 304 (on the detector side of the scanner axis). The path of z-ray A with respect to edge 312 can be more clearly seen in FIG. 4(c), to be described later on. (Note, the term "z-ray" is used herein simply to facilitate the description of the drawings and is not a conventional term of art nor is it a new type of radiation.) As illustrated, z-rays A, B, C, and D are the limiting "z-rays" which define the dose profile for a square x-ray beam spot profile. In practice, the adjustment of beam spot position on target 302 is made for a set of "z-rays" which is tangential to the specification circle (radius $R_{SP}$ as shown in FIG. 4a) and out of the plane of the illustration of FIG. 3. The beam spot position and corresponding beam radius on the target are thus functions which are varied in accordance with the desired slice width. The different beam radii result from the 82° angulation of target 302 with respect to the z-axis of the scanner.

Also in the preferred embodiment, an adjustable radiation shield 314 is located on the detector side of septum 300 and is adjusted so as to minimize scattered radiation. This shield serves as a post-patient collimator, and in this function its end face which faces septum 300 operates to block the x-ray fan beam in a manner similar to the x-ray blocking provided by end face 310 of collimator ring 308. In operation, radiation shield 314 is adjusted toward septum 300 to the point where it is just about to impinge upon z-ray D. If desired, radiation shield 314 may also be used to define the slice width. A fixed position radiation shield 316 is also shown attached to septum 300 on its detector side.

The adjustable collimator ring 308 and adjustable radiation shield 314 are typically constructed of brass and may be similar or even identical. Each ring may be controllably positionable so its longitudinal axis is exactly coaxial with the scanner z-axis by means of three motor-driven screws coupled between each ring and a support housing. The support housing, shown in detail in FIG. 5, is positioned adjacent the end face of conical portion 6 of the scanner. The screws may be controlled so as to be turned together, or may also be adjusted individually to ensure that the end face planes of rings 308 and 314 are exactly perpendicular to the scanner z-axis (and therefore parallel to septum 300).

FIG. 4a is a schematic representation of the front view of the scanner gantry showing the relative positions of the target, detector and collimator rings, and illustrating as well the radii of the scan ($R_{SC}$) and specification circles ($R_{SP}$). $R_C$ and $R_T$ illustrate the collimator and target radii, respectively. The z-rays which are tangential to the specification circle at pixel P are also shown.

FIG. 4b is a projection of the collimator system geometry in the -z-direction for the rays through pixel P. Note, FIG. 4b is drawn as if both sides of the collimator are in the detector/target overlap region, that is, that region wherein a portion of the detector array 8 and the target ring 302 overlap, region "O". Z-rays A, B, C, and D are limiting "z-rays" which define the dose profile for a square x-ray beam spot profile b. The position of the x-ray beam spot along a radial portion b of target ring 302, as well as the proximity of collimator ring 308 to the fixed septum 300, establishes a dose profile at point P on the specification circle, as illustrated.

The slot width 306 is selected by simple geometry to give the required slice width on the axis for radial rays. The septum thickness t, is chosen to give sufficient separation of the detector and septum to contain the necessary radiation shields. As explained above, "z-ray" A (at the specification circle) is used to set-up the required geometry (beam spot position) for a desired slice thickness.

FIG. 4c shows the typical loci of the "z-rays" A, B, C and D at the septum aperture radius (edge 312) on the detector-side of septum 300 for rays which span the scan circle $R_{SC}$. As shown, outside the specification circle $R_{SP}$, "z-ray" A is blocked by edge 312 of the septum. This can be visualized by imagining a light beam projected from the x-ray beam spot b of FIG. 4b up through the collimator slot so that a cone of light would form the pattern of z-rays which would strike detector array 8. The portions of the septum which are both into and out of the plane illustrated in FIG. 4b provide the curved shape to the cone of the rays which appear on the detector side of the collimator. This curvature of the rays is illustrated more clearly in the view shown in FIG. 4c for each of the z-rays A, B, C and D. Due to this curvature, which results from the geometry of the hole in septum 300, the dose profile linearly increases from the edge of the septum to the point wherein the z-rays no longer impinge any part of collimator ring 308 or septum 300, and then proceed unimpeded from target 302 to detector array 8. This condition corresponds to those z-rays between rays B and C. Thus, the dose profile at the scan circle is shown as a trapezoid, such as illustrated in FIGS. 4b and 4c. As shown in FIG. 4c, ray A is blocked by the septum outside the specification circle. This configuration is chosen to satisfy the condition of 100% efficiency inside the specification circle with a minimum cone angle. The blocked dose reaches a maximum value at the scan circle. Note, z-rays B, C and D are not blocked by the collimator at any point.

As apparent from the prior Figures, mechanical attachment of septum 300 to the scanner housing cannot be accomplished by any connection to the septum in the area where the target and detector array overlap, i.e., region 0. However, in the detector-only region (the top portion of FIG. 4a), the collimator slot area (i.e., on the target side of septum 300) can be filled-in, since it's not needed for collimation, while in the target-only region, the detector slot area (i.e., on the detector side of septum 300) can be filled-in. Thus, referring now to FIG. 5 which illustrates a cross-section of the novel collimator arrangement, a preferred location for attachment of the septum to the scanner housing is by connection to the detector side of septum 300 in the vicinity of the target (support housing 504, as shown in FIG. 5b), and on the target side of the septum in the vicinity of the detector array (support housing 502, as shown in FIG. 5c). As shown in FIGS. 5(a) and (c), support housings 502 and 504 are held together by a common bolt arrangement 506 attached to the scanner housing, from which they are both suspended. The forenoted motor driven screws which controllably position the collimator ring 308 and detector shield 314 with respect to septum 300, are partially illustrated in FIG. 5(a), as arrangements 508 and 510 provided between support housings 502 and 504, respectively. Each ring includes three of these screw arrangements, each spaced 120° apart.

An illustrative geometry is as follows (all dimensions are in millimeters unless stated to be otherwise):

| | | |
|---|---|---|
| Detector radius | 675 | |
| 100% effic. circle radius | 250 | |
| Collimator radius | 375 | |
| Radiation shield radius | 375 | |
| Septum width (t) | 1.50 | |
| X-ray beam spot length | 2.50 | |
| Target angle | 78 deg. | |
| Nominal slice width | 3 | 6 |
| Electron beam radius on target | 882.4 | 900 |
| Collimator slot width | 1.725 | 3.500 |
| z, beam spot center | +6.24 | +9.98 |
| z, slice center on z-axis | −3.11 | −4.13 |

Thus, there has been shown and described a novel collimator for an electron beam CT scanner which satisfies all the objects and advantages sought therefore. Many changes, modifications, variations and other uses and applications of the subject invention will, however, become apparent to those skilled in the art after considering this specification and its accompanying drawings, which disclose preferred embodiments thereof. For example, many of the mechanical details, especially those relating to the support of septum 300, are subject to modification, depending on the specific application, which applications are not limited to medical scanners, but also include, e.g., industrial and non-destructive testing devices. Furthermore, as used herein with respect to rings 302, 308 and 314, it should be clear that circular or "ring-shaped" is intended to include part-circular or part ring-shaped, and even part-curvilinear shapes other than those having a fixed radius, which other shapes may be useful in other types of modified scanner designs. Still further, it should be clear that the diameter of rings 308 and 314 could be modified to be greater or less than that of aperture 304 and still be useful. It should also be clear that the aperture alone in septum 300 can supply the needed collimation of the x-rays, the ring 308 being used in the preferred medical scanner embodiment as a pre-patient shield to reduce exposure of the patient to radiation and to reduce scattered radiation. All such changes, modifications, variations and other uses and applications which do not depart from the spirit and scope of the invention are deemed to be covered by this patent, which is limited only by the claims which follow as interpreted in light of the foregoing description.

We claim:

1. A method for collimating a rotating fan beam of x-rays, comprising:
   providing a fixed position planar septum between a moving source of x-rays and a fixed position detector array for said x-rays, said septum being substantially parallel with respect to a plane described by said moving source of x-rays so as to define a source side and a detector side for said septum, said septum having an aperture therein through which a portion of said x-rays pass on their way from said source of x-rays to the detector array;
   providing an adjustable-position ring having an end face positioned in a plane substantially parallel with but spatially offset from the source side of said septum and having a longitudinal axis which is substantially coaxial with an axis of symmetry of said aperture; and
   controlling the offset between said ring and said septum for adjusting the collimation width of said x-rays.

2. The method of claim 1, further including the step of:
   controlling said space between the plane of said moving source of x-rays and the target side of said septum simultaneously with control of said offset, so as to maximize the collimator efficiency and minimize the cone angle between the x-ray fan beam and the said septum.

3. An electron beam computed tomography scanner, comprising:
   a source for generating an electron beam;
   a ring-shaped target positioned a given distance from said source;
   deflection means for causing said electron beam to scan along said target as a spot, thereby creating in response thereto a moving source of x-rays, which movement describes a plane;
   a ring-shaped x-ray detector array positioned in a plane substantially parallel with the plane of said moving source of x-rays and spaced therefrom in an overlapping and opposing manner; and
   a collimator arrangement positioned in the space between said target and said detector array for collimating the moving source of x-rays as received at said detector array, said collimator arrangement comprising:
   a fixed position septum formed of an x-ray blocking material and having an aperture therein, said septum oriented substantially parallel to the planes of said moving source of x-rays and detector array, so as to define a target side and a detector side for said septum, which septum blocks the passage of x-rays from said target to said detector array except for those x-rays passing through said aperture; and
   an adjustable-position collimator ring having a longitudinal axis located co-axially with the aperture in the septum and adjustable towards/away from the target side of said septum so as to controllably define a slot for said x-rays as viewed from said moving source of x-rays on said target, said slot being defined by the space between an end of said adjustable-position collimator ring which faces said septum, and the aperture of said septum.

4. A scanner as defined by claim 3, further including:
   an evacuated part-conical shaped envelope having an elongated axis, for enclosing said source, target and deflection means, said source being positioned at a narrow end of said envelope and said target being positioned at an opposing wide end;
   said septum being positioned adjacent said wide end so that the plane of the septum is substantially perpendicular to the elongated axis of said envelope.

5. A scanner as defined by claim 4, further including:
   a support housing positioned adjacent said wide end of said evacuated envelope, said support housing including first and second ring-shaped support frames positioned in a closely-spaced opposed manner and forming a space therebetween, each support frame having an aperture therein having a diameter which is greater than the diameter of the aperture in said septum and a center point which is substantially coincident with the center point of the aperture in said septum.

6. A scanner as defined by claim 5, wherein a portion of the target side of said septum which is in the vicinity of said detector array is attached to said first support frame and a portion of the detector side of said septum which is in the vicinity of said target is attached to said second support frame.

7. A scanner as defined by claim 6, wherein the longitudinal axis of said adjustable-position collimator ring is positioned to be co-axial with the elongated axis of said envelope by an adjustable coupling of said collimator ring to said first support frame.

8. A scanner as defined by claim 6, further including:
   a post-collimator radiation shield comprising an adjustable position ring having a longitudinal axis located co-axially with the aperture in the septum and adjustable towards/away from the detector side of said septum.

9. A scanner as defined by claim 5, further including:
   an adjustable-position ring-shaped radiation shield having a longitudinal axis located co-axially with the aperture in the septum and adjustable towards/away from the detector side of said septum.

10. A scanner as defined by claim 9, wherein the longitudinal axis of said adjustable-position radiation shield is positioned to be co-axial with the elongated axis of said envelope by an adjustable coupling of said radiation shield to said second support frame.

11. A scanner as defined by claim 3, further including:
    control means coupled to said deflection means and said collimator ring, for controlling said deflection means so as to change the radial position of said spot scanned on said target in a coordinated manner with a change in the position of said collimator ring, so as to thereby change the width of said fan beam.

12. A scanner as defined by claim 3, further including:
    an adjustable-position ring-shaped radiation shield having a longitudinal axis located co-axially with the aperture in the septum and adjustable towards/away from the detector side of said septum.

13. A scanner as defined by claim 3, wherein:
    said aperture and collimator ring are circularly shaped, and the outside diameter of said adjustable-position collimator ring and the diameter of said aperture in said septum are substantially the same.

14. An electron beam computed tomography scanner, comprising:
- a source for generating an electron beam;
- a ring-shaped target positioned a given distance from said source;
- deflection means for causing said electron beam to scan along said target as a spot, thereby creating in response thereto a moving source of x-rays, which movement describes a plane;
- a ring-shaped x-ray detector array positioned in a plane substantially parallel with the plane of said moving source of x-rays and spaced therefrom in an overlapping and opposing manner; and
- a collimator arrangement positioned in the space between said target and said detector array for collimating the moving source of x-rays as received at said detector array, said collimator arrangement comprising:
- a fixed position septum formed of an x-ray blocking material and having an aperture therein, said septum oriented substantially parallel to the planes of said moving source of x-rays and detector array, so as to define a target side and a detector side for said septum, which septum blocks the passage of x-rays from said target to said detector array except for those x-rays passing through said aperture; and
- control means coupled to said deflection means for controlling said deflection means so as to change the radial position of said spot scanned on said target so as to thereby change the width of said fan beam which reaches said detector.

15. Apparatus for collimating a moving fan beam of x-rays, comprising:
- a fixed position x-ray blocking septum located in the space between a source of said moving x-ray beam and an x-ray detector array for detecting said X-rays, said septum being positioned substantially parallel to a plane described by the moving source, so as to divide said space into target and detector sections, respectively, said target section including said source of moving x-ray beam and said detector section including said x-ray detector array, said septum having an aperture therein through which a portion of said x-rays pass from said source to said detector array, thereby collimating said x-rays;
- an adjustable-position ring located in said target section and having an end face positioned in a plane substantially parallel with, but spatially offset from, said septum and having a center point which is substantially coincident with a center point of said aperture; and
- means for controlling the offset between said ring and said septum for adjusting the collimation width of said x-ray beam.

16. Apparatus as defined by claim 15, further including:
- an adjustable-position ring-shaped radiation shield located in said detector section and having an end face positioned in a plane substantially parallel with, but spatially offset from, said septum and having a longitudinal axis located co-axially with the aperture in the septum and adjustable towards/away from the detector side of said septum.

17. Apparatus as defined by claim 15, further including:
- deflection means for controlling a space between said source of moving x-ray beam and said septum, thereby controlling the width of said fan beam.

18. A method for collimating a rotating fan beam of x-rays, comprising:
- providing a fixed position planar septum between a moving source of x-rays and a fixed position detector array for said x-rays, said septum being substantially parallel with respect to a plane described by said moving source of x-rays so as to define a source side and a detector side for said septum, said septum having an aperture therein through which a portion of said x-rays pass on their way from said source of x-rays to the detector array; and
- controlling a space between the plane of said moving source of x-rays and the target side of said septum for controlling the width of said fan beam.

* * * * *